(12) United States Patent
Bolli et al.

(10) Patent No.: US 8,044,076 B2
(45) Date of Patent: Oct. 25, 2011

(54) PHENYL DERIVATIVES AND THEIR USE AS IMMUNOMODULATORS

(75) Inventors: Martin Bolli, Allschwil (CH); David Lehmann, Galmiz (CH); Boris Mathys, Pratteln (CH); Claus Mueller, Weil am Rhein (DE); Oliver Nayler, Arlesheim (CH); Beat Steiner, Domach (CH); Jorg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 75 days.

(21) Appl. No.: 12/442,203

(22) PCT Filed: Jul. 10, 2007

(86) PCT No.: PCT/IB2007/052746
§ 371 (c)(1),
(2), (4) Date: Mar. 20, 2009

(87) PCT Pub. No.: WO2008/035239
PCT Pub. Date: Mar. 27, 2008

(65) Prior Publication Data
US 2010/0087495 A1    Apr. 8, 2010

(30) Foreign Application Priority Data
Sep. 21, 2006   (WO) .................. PCT/IB2006/053426

(51) Int. Cl.
*A61K 31/535* (2006.01)
(52) U.S. Cl. ....................................... 514/364; 548/131
(58) Field of Classification Search .................. 514/364; 548/131
See application file for complete search history.

(56) References Cited

U.S. PATENT DOCUMENTS

| | | |
|---|---|---|
| 2007/0043104 A1 | 2/2007 | Luthman et al. |
| 2007/0270438 A1 | 11/2007 | Bhattacharya et al. |
| 2008/0249093 A1 | 10/2008 | Colandrea et al. |
| 2008/0306124 A1 | 12/2008 | Albert et al. |
| 2010/0063108 A1 | 3/2010 | Bolli et al. |
| 2010/0087417 A1 | 4/2010 | Bolli et al. |
| 2010/0168005 A1 | 7/2010 | Bolli et al. |
| 2010/0234346 A1 | 9/2010 | Bolli et al. |
| 2010/0331372 A1 | 12/2010 | Bolli et al. |
| 2011/0028448 A1 | 2/2011 | Bolli et al. |
| 2011/0028449 A1 | 2/2011 | Bolli et al. |
| 2011/0046170 A1 | 2/2011 | Bolli et al. |

FOREIGN PATENT DOCUMENTS

| | | |
|---|---|---|
| WO | WO 91/15583 | 10/1991 |
| WO | WO 99/46277 | 9/1999 |
| WO | WO 01/12627 | 2/2001 |
| WO | WO 02/068417 | 9/2002 |
| WO | WO 2003/062248 | 7/2003 |
| WO | WO 03/105771 | 12/2003 |
| WO | WO 2004/035538 | 4/2004 |
| WO | WO 2004/103279 | 12/2004 |
| WO | WO 2005/014525 | 2/2005 |
| WO | WO 2005/032465 | 4/2005 |
| WO | WO 2005/058848 | 6/2005 |
| WO | WO 2005/115382 | 12/2005 |
| WO | WO 2006/100631 | 9/2006 |
| WO | WO 2006/114400 | 11/2006 |
| WO | WO 2006/131336 | 12/2006 |
| WO | WO 2007/001973 | 1/2007 |
| WO | WO 2007/085451 | 8/2007 |
| WO | WO 2007/132307 | 11/2007 |
| WO | WO 2008/029370 | 3/2008 |
| WO | WO 2008/029371 | 3/2008 |
| WO | WO 2008/037476 | 4/2008 |
| WO | WO 2008/076356 | 6/2008 |
| WO | WO 2008/091967 | 7/2008 |

OTHER PUBLICATIONS

Patani et al "Bioisosterism: A rational approach in drug design", Chem. Rev. 1996, vol. 96, No. 8, pp. 3147-3176.*

Kiryanov, A., et al., Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis, Journal of Organic Chemistry, 2001, pp. 7925-7929, vol. 66.

Chakraborti, et al., One-Pot Synthesis of Nitriles from Aldehydes Under Microwave Irradiation: Influence of the Medium and Mode of Microwave Irradiation on Product Formation, Tetrahedron, 1999, pp. 13265-13268, vol. 55.

Kaboudin, K., et al, One-Pot Synthesis of 1,2,4-Oxadiazoles Mediated by Microwave Irradiation under Solvent-Free Condition, Heterocycles, 2003, pp. 2287-2292, vol. 60, No. 10.

Brain, C.T., et al., Novel Procedure for the Synthesis of 1,3,4-Oxadiazoles from 1,2-diacylhydrazinos Using Polymer-Supported Burgess Reagent under Microwave Conditions, Tetrahedron Letters, 1999, pp. 3275-3278, vol. 40.

John, E.O., et al., Reactions of (Difluoroamino) Difluoroacetonitrile and (Difluoroamino) Difluoroacetamidoxime, Inorganic Chemistry, 1988, pp. 3100-3104, vol. 27.

(Continued)

*Primary Examiner* — Brandon Fetterolf
*Assistant Examiner* — Jean Cornet
(74) *Attorney, Agent, or Firm* — Hoxie & Associates LLC

(57) ABSTRACT

The invention relates to phenyl derivatives of formula (I), their preparation and their use as pharmaceutically active compounds. Said compounds particularly act as immuno-modulating agents.

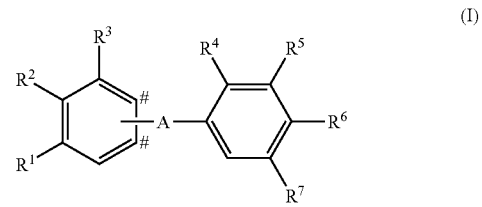

19 Claims, No Drawings

OTHER PUBLICATIONS

Ecke, et al., Ortho-Alkylation of Aromatic Amines, Journal of Organic Chemistry, 1957, pp. 639-642, vol. 22.

Xu, B., et al., Acyclic Analogues of Adenosine Biphosphates as P2Y Receptor Antagonists: Phosphate Substitution Leads to Multiple Pathways of Inhibition of Platelet Aggregation, Journal of Medicinal Chemistry, 2002, pp. 5694-5709, vol. 45.

Gangloff, et al., Synthesis of 3,5-disubstituted-1,2,4-Oxadiazoles Using Tetrabutylammonium Fluoride as a Mild and Efficient Catalyst, Tetrahedron Letters, 201, pp. 1441-1443, vol. 42.

Gibson, M. (Editor), Pharmaceutical Preformuiation and Formulation, HIS Health Group, Englewood, CO, USA, (2001).

Greene, T.W., et al., Protective Groups in Organic Synthesis, $3^{rd}$ Edition, Wiley New York, (1991).

Hla, et al., An Abundant Transcript Induced in Differentiating Human Endothelial Cells Encodes a Polypeptide with Structural Similarities to G-Protein-Coupled-Receptors, The Journal of Biological Chemistry, 1990, pp. 9308-9313, vol. 265, No. 16, The Medical Society for Biochemistry and Molecular Biology, Inc., USA.

Gould, P.L., Salt Selection for Basic Drugs, International Journal of Pharmaceutics, 1986, pp. 201-217, vol. 33.

Cui, J., et al., Design and Synthesis of Highly Constrained Factor Xa Inhibitors: Amidine-Substituted Bis(benzoyl)-[1,3]-diazepan-2-ones and Bis(benzylidene)-bis(gem-dimethyl)Cycloketones, Bioorganic Medicinal Chemistry, 2003, pp. 3379-3392, vol. 11.

Garcia, M.A., et al., Synthesis, Biological Evaluation, and Three-Dimensional Quantitative Structure—Activity Relationship Study of Small-Molecule Positive Modulators of Adrenomedullin, Journal of Medicinal Chemistry, 2005, pp. 4068-4075, vol. 48.

Meyer, E., et al., Synthesis of New 1,2,4- and 1,3,4-Oxadiazole Derivatives, Synthesis, 2003, pp. 899-905, No. 6.

Sato, N., et al., Synthesis and evaluation of substituted 4-alkoxy-2-aminopyridines as novel neuropeptide Y1 receptor antagonists, Bioorganic and Medicinal Chemistry Letters, 2004, pp. 1761-1764, vol. 14.

Kocienski, P.J., Protecting Groups, Thiome Stuggart, 1994.

Glennon, R.A., et al., β-Oxygenated Analogues of the 5-HT2A Serotonin Receptor Agonist 1-(4-Bromo-2,5-dimethoxyphenyl)-2-aminopropane, Journal of Medicinal Chemistry, 2004, pp. 6034-6041, vol. 47.

Poulain, R.F., et al., Parallel synthesis of 1,2,4-oxadiazoles from carboxylic acids using an improved, uronium-based, activation, Tetrahedron Letters, 2001, pp. 1495-1499, vol. 42.

Srivastava, R.M., et al., Synthesis of 3-Aryl-5-[Thien-3-YL Methyl]-1,2,4-Oxadiazoles, Synthetic Communications, 1999, pp. 1437-1450, vol. 29.

Gennaro, A.R. (Chairman of the Editorial Board and Editor-)Remington, The Science and Practice of Pharmacy, $20^{th}$ Edition, Philadelphia College of Pharmacy and Science.

Suzuki, T., et al., Synthesis of the Selective 5-Hydroxytryptamine 4 (5-$HT_4$) Receptor Agonist (+)-(S)-2-Chloro-5-methoxy-4[5-(2-piperydylmethyl)-1,2,4-oxadiazol-3-yl]antline, Chem. Pharm. Bull., 1999, pp. 120-122, vol. 47.

Trapani, G., et al., Propofol Analogues. Synthesis, Relationships between Structure and Affinity at GABAA Receptor in Rat Brain, and Differential Electrophysiological Profile at Recombinant Human GABAA Receptors, Journal of Medicinal Chemistry, 1998, pp. 1846-1854, vol. 41.

Yan, L., et al., Discovery of 3-arylpropionic acids as potent agonists of sphingosine-1-phosphate receptor-1 (S1P1) with high selectivity against all other known S1P receptor subtypes, Bioorganic and Medicinal Chemistry Letters, 2006, pp. 3679-3683, vol. 16, No. 14.

Zhen, L., et al., Discovery of Potent 3,5-Diphenyl-1,2,4-oxadiazole Sphingosine-1-phosphate-1 (S1P1) Receptor Agonists with Exceptional Selectivity against S1P2 and S1P, Journal of Medicinal Chemistry, 2005, pp. 6169-6173, vol. 48, No. 20.

U.S. Appl. No. 12/673,918.

* cited by examiner

PHENYL DERIVATIVES AND THEIR USE AS IMMUNOMODULATORS

CROSS REFERENCE TO RELATED APPLICATIONS

This application is a United States National Stage Application under 35 U.S.C. 371 of PCT/IB2007/052746 filed on Jul. 10, 2007, which claims the benefit of PCT/IB2006/053426 filed on Sep. 21, 2006, the contents of each of which are incorporated herein by reference in their entirety.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term $C_{1-5}$-alkyl, alone or in combination with other groups, means saturated, branched or straight chain groups with one to five carbon atoms. Preferred examples of $C_{1-5}$-alkyl groups are methyl, ethyl, n-propyl, iso-propyl, n-butyl, iso-butyl, n-pentyl, and iso-pentyl.

Likewise, the term $C_{1-4}$-alkyl, alone or in combination with other groups, means saturated, branched or straight chain groups with one to four carbon atoms. Preferred examples of $C_{1-4}$-alkyl groups are methyl, ethyl, n-propyl, iso-propyl, n-butyl, and iso-butyl.

Likewise, the term $C_{1-3}$-alkyl, alone or in combination with other groups, means saturated, branched or preferably straight chain groups with one to three carbon atoms and represents a methyl, ethyl, n-propyl, or iso-propyl group.

Likewise, the term $C_{2-5}$-alkyl, alone or in combination with other groups, means saturated, branched or straight chain groups with two to five carbon atoms. Preferred examples of $C_{2-5}$-alkyl groups are ethyl, n-propyl, iso-propyl, n-butyl, iso-butyl, n-pentyl, and iso-pentyl.

Likewise, the term $C_{2-4}$-alkyl, alone or in combination with other groups, means saturated, branched or straight chain groups with two to four carbon atoms. Preferred examples of $C_{2-4}$-alkyl groups are ethyl, n-propyl, iso-propyl, n-butyl, and iso-butyl.

The term $C_{1-4}$-alkoxy, alone or in combination with other groups, means an R-0 group, wherein R is a $C_{1-4}$-alkyl. Preferred examples of $C_{1-4}$-alkoxy groups are ethoxy, propoxy, iso-propoxy, and iso-butoxy.

The term $C_{1-3}$-alkoxy, alone or in combination with other groups, means an R-0 group, wherein R is a $C_{1-3}$-alkyl.

Likewise, the term $C_{2-5}$-alkoxy, alone or in combination with other groups, means an R—O group, wherein R is a $C_{2-5}$-alkyl. Preferred examples of $C_{2-5}$-alkoxy groups are ethoxy, propoxy, iso-propoxy, iso-butoxy, and iso-pentoxy.

The term halogen means fluoro, chloro, bromo or iodo, preferably fluoro or chloro. Salts are preferably the pharmaceutically acceptable salts of the compounds of Formula (I).

The term "pharmaceutically acceptable salts" refers to non-toxic, inorganic or organic acid and/or base addition salts, Lit.: e.g. "Salt selection for basic drugs", *Int. J. Pharm.* (1986), 33, 201-217.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

i) The invention relates to novel phenyl compounds of the Formula (I),

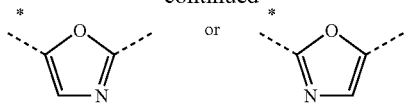

Formula (I)

wherein the symbol # indicates the two carbon atoms of the phenyl ring bearing $R^1$, $R^2$ and $R^3$ to either of which the group A may be attached; and wherein A represents

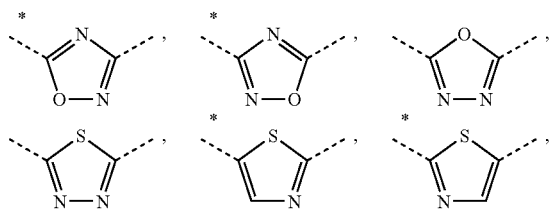

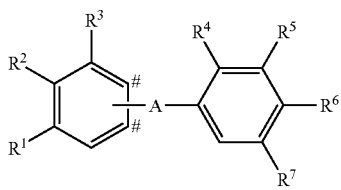

wherein the asterisks indicate the bond that is linked to the phenyl ring of Formula (I) bearing $R^1$, $R^2$, and $R^3$;

$R^1$ represents hydrogen, $C_{1-3}$-alkyl, fluoro, chloro, methoxy, or cyano;

$R^2$ represents $C_{2-5}$-alkyl or $C_{1-4}$-alkoxy;

$R^3$ represents hydrogen, and in case the group A is attached to the para-position with respect to $R^2$ of the phenyl ring of Formula (I) bearing $R^1$, $R^2$ and $R^3$, $R^3$ may in addition represent a methyl group;

$R^4$ represents hydrogen, $C_{1-3}$-alkyl, $C_{1-3}$-alkoxy, or halogen;

$R^5$ represents hydrogen, $C_{1-3}$-alkyl, $C_{1-3}$-alkoxy, or halogen;

$R^6$ represents hydroxy-$C_{1-5}$-alkyl, 2,3-dihydroxypropyl, di-(hydroxy-$C_{1-4}$-alkyl)-$C_{1-4}$-alkyl, —$CH_2$—$(CH_2)_k$—$NR^{61}R^{62}$, —$(CH_2)_n$CH(OH)—$CH_2$—$NR^{61}R^{62}$, —$CH_2$—$(CH_2)_n$—$NHSO_2R^{63}$, —$(CH_2)_n$CH(OH)—$CH_2$—$NHSO_2R^{63}$, —$CH_2$—$(CH_2)_n$—$NHCOR^{64}$, —$(CH_2)_n$CH(OH)—$CH_2$—$NHCOR^{64}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NR^{61}R^{62}$, —$OCH_2$—CH(OH)—$CH_2$—$NR^{61}R^{62}$, —$OCH_2$—$(CH_2)_m$—$NHSO_2R^{63}$, —$OCH_2$—CH(OH)—$CH_2$—$NHSO_2R^{63}$, —$OCH_2$—$(CH_2)_m$—$NHCOR^{64}$, or —$OCH_2$—CH(OH)—$CH_2$—$NHCOR^{64}$;

$R^{61}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;

$R^{62}$ represents hydrogen, methyl, or ethyl;

$R^{63}$ represents $C_{1-3}$-alkyl, methylamino, ethylamino, or dimethylamino;

$R^{64}$ represents hydroxymethyl, 2-hydroxyethyl, 2-hydroxy-1-hydroxymethyl-ethyl, or 2,3-dihydroxypropyl;

k represents the integer 1, 2, or 3;

m represents the integer 1 or 2;

n represents 0, 1, or 2; and $R^7$ represents hydrogen, $C_{1-3}$-alkyl, or halogen;

and salts thereof.

ii) A particular embodiment of the invention relates to phenyl derivatives according to embodiment i), wherein A represents

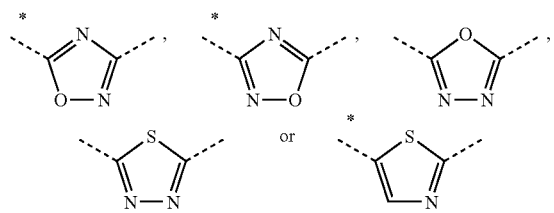

wherein the asterisks indicate the bond that is linked to the phenyl ring of Formula (I) bearing $R^4$, $R^2$, and $R^3$, and salts thereof.

iii) Another particular embodiment of the invention relates to phenyl derivatives according to embodiment i), wherein A represents

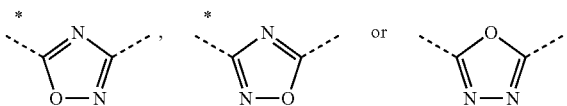

wherein the asterisks indicate the bond that is linked to the phenyl ring of Formula (I) bearing $R^1$, $R^2$, and $R^3$, and salts thereof.

iv) Another particular embodiment of the invention relates to phenyl derivatives according to embodiment i), wherein A represents

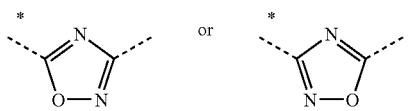

wherein the asterisks indicate the bond that is linked to the phenyl ring of Formula (I) bearing $R^1$, $R^2$, and $R^3$, and salts thereof.

v) Another particular embodiment of the invention relates to phenyl derivatives according to embodiment i), wherein A represents

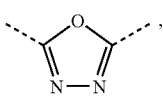

and salts thereof.

vi) A preferred embodiment of the invention relates to phenyl derivatives according to any one of the embodiments i) to v), wherein $R^1$ represents a methyl group, and salts thereof.

vii) Another preferred embodiment of the invention relates to phenyl derivatives according to any one of the embodiments i) to vi), wherein $R^2$ represents n-propyl, n-butyl, isobutyl, isoamyl, propoxy or isopropoxy, and salts thereof.

viii) Another preferred embodiment of the invention relates to phenyl derivatives according to any one of the embodiments i) to vi), wherein $R^2$ represents isobutyl or isopropoxy, and salts thereof.

ix) A preferred embodiment of the invention relates to phenyl derivatives according to any one of the embodiments i) to viii), wherein $R^3$ represents hydrogen, and salts thereof.

x) Another preferred embodiment of the invention relates to phenyl derivatives according to any one of the embodiments i) to ix), wherein $R^4$ represents hydrogen, $R^5$ represents methyl, ethyl, or methoxy, and $R^7$ represents methyl, ethyl, or halogen, and salts thereof.

xi) Another preferred embodiment of the invention relates to phenyl derivatives according to any one of the embodiments i) to ix), wherein $R^4$ represents hydrogen, and $R^5$ and $R^7$ represent a methyl group, and salts thereof.

xii) A particularly preferred embodiment of the invention relates to phenyl derivatives according to any one of the embodiments i) to ix), wherein $R^4$ represents hydrogen, $R^5$ represents a methyl group, and $R^7$ represents an ethyl group, and salts thereof.

xiii) Another preferred embodiment of the invention relates to phenyl derivatives according to any one of the embodiments i) to ix), wherein $R^4$ represents hydrogen, $R^5$ represents a methoxy group, and $R^7$ represents a chlorine atom, and salts thereof.

xiv) Another preferred embodiment of the invention relates to phenyl derivatives according to any one of the embodiments i) to xiii), wherein $R^6$ represents hydroxy-$C_{1-5}$-alkyl, 2,3-dihydroxypropyl, —$CH_2$—$(CH_2)_k$—$NR^{61}R^{62}$, —$(CH_2)_n$CH(OH)—$CH_2$—$NR^{61}R^{62}$, —$CH_2$—$(CH_2)_n$—$NHCOR^{64}$, —$(CH_2)_n$CH(OH)—$CH_2$—$NHCOR^{64}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NR^{61}R^{62}$, —$OCH_2$—CH(OH)—$CH_2$—$NR^{61}R^{62}$, —$OCH_2$—$(CH_2)_m$—$NHSO_2R^{63}$, —$OCH_2$—CH(OH)—$CH_2$—$NHSO_2R^{63}$, —$OCH_2$—$(CH_2)_m$—$NHCOR^{64}$, or —$OCH_2$—CH(OH)—$CH_2$—$NHCOR^{64}$, and salts thereof.

xv) Another preferred embodiment of the invention relates to phenyl derivatives according to any one of the embodiments i) to xiii), wherein $R^6$ represents hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NHCOR^{64}$, or —$OCH_2$—CH(OH)—$CH_2$—$NHCOR^{64}$, and salts thereof.

xvi) Another preferred embodiment of the invention relates to phenyl derivatives according to any one of the embodiments i) to xiii), wherein $R^6$ represents 3-hydroxy-2-hydroxymethyl-propoxy, 2,3-dihydroxypropoxy, or —$OCH_2$—CH(OH)—$CH_2$—$NHCOR^{64}$, and salts thereof.

xvii) Another preferred embodiment of the invention relates to phenyl derivatives according to any one of the embodiments i) to xiii), wherein $R^6$ represents —$OCH_2$—CH(OH)—$CH_2$—$NHCOR^{64}$, and $R^{64}$ represents hydroxymethyl, and salts thereof.

xviii) Another preferred embodiment of the invention relates to phenyl derivatives according to any one of the embodiments i) to xvii), wherein the group A is attached at the para position with respect to $R^2$ to the phenyl ring of Formula (I) bearing $R^1$, $R^2$ and $R^3$, and salts thereof.

xix) An especially preferred embodiment of the invention relates to phenyl derivatives according to embodiment i), wherein A represents

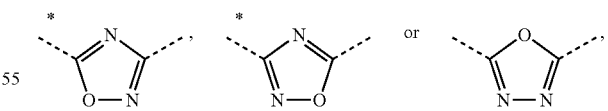

wherein the asterisks indicate the bond that is linked to the phenyl ring of Formula (I) bearing $R^1$, $R^2$ and $R^3$; $R^1$ represents methyl; $R^2$ represents isobutyl or isopropoxy; $R^3$ represents hydrogen; $R^4$ represents hydrogen or methoxy; $R^5$ represents hydrogen, methyl, ethyl or methoxy; $R^6$ represents 3-hydroxy-2-hydroxymethyl-propoxy, 2,3-dihydroxypropoxy, or —$OCH_2$—CH(OH)—$CH_2$—$NHCOR^{64}$; and $R^7$ represents hydrogen, methyl, ethyl or chlorine; and salts thereof.

xx) Another very preferred embodiment of the invention relates to phenyl derivatives according to embodiment i), wherein A represents

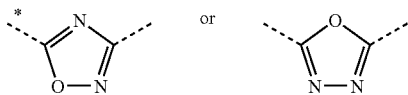

wherein the asterisk indicates the bond that is linked to the phenyl ring of Formula (I) bearing $R^1$, $R^2$, and $R^3$;
$R^1$ represents hydrogen or $C_{1-3}$-alkyl;
$R^2$ represents $C_{2-5}$-alkyl or $C_{1-4}$-alkoxy;
$R^3$ represents hydrogen, and in case the group A is attached to the para-position with respect to $R^2$ of the phenyl ring of Formula (I) bearing $R^1$, $R^2$ and $R^3$, $R^3$ may in addition represent a methyl group;
$R^4$ represents hydrogen;
$R^5$ represents $C_{1-3}$-alkyl;
$R^6$ represents hydroxy, 2,3-dihydroxypropoxy, —OCH$_2$—CH(OH)—CH$_2$—NR$^{61}$R$^{62}$, or —OCH$_2$—CH(OH)—CH$_2$—NHCOR$^{64}$;
$R^{61}$ and $R^{62}$ both represent hydrogen;
$R^{64}$ represents hydroxymethyl; and
$R^7$ represents $C_{1-3}$-alkyl;
and salts thereof.
xxi) Especially preferred phenyl compounds according to Formula (I) are:
2-hydroxy-N-((2R)-2-hydroxy-3-{4-[5-(4-isopropoxy-3-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isopropoxy-3-methyl-phenyl)-[1,2,4]oxadiazol-3-yl]-2,6-dimethyl-phenoxy}-propyl)-acetamide,
N-((2R)-3-{2-ethyl-4-[5-(4-isopropoxy-3-methyl-phenyl)-[1,2,4]oxadiazol-3-yl]-6-methyl-phenoxy}-2-hydroxy-propyl)-2-hydroxy-acetamide,
N-((2S)-3-{2-ethyl-4-[5-(4-isopropoxy-3-methyl-phenyl)-[1,2,4]oxadiazol-3-yl]-6-methyl-phenoxy}-2-hydroxy-propyl)-2-hydroxy-acetamide,
2-hydroxy-N-((2R)-2-hydroxy-3-{4-[5-(3-isopropoxy-4-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(3-isopropoxy-4-methyl-phenyl)-[1,2,4]oxadiazol-3-yl]-2,6-dimethyl-phenoxy}-propyl)-acetamide,
2-hydroxy-N-((2R)-2-hydroxy-3-{4-[5-(4-isobutyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isobutyl-phenyl)-[1,2,4]oxadiazol-3-yl]-2,6-dimethyl-phenoxy}-propyl)-acetamide,
2-hydroxy-N-((2R)-2-hydroxy-3-{4-[5-(4-isobutyl-3-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isobutyl-3-methyl-phenyl)-[1,2,4]oxadiazol-3-yl]-2,6-dimethyl-phenoxy}-propyl)acetamide,
N-((2R)-3-{2-ethyl-4-[5-(4-isopropoxy-3-methyl-phenyl)-[1,3,4]oxadiazol-2-yl]-6-methyl-phenoxy}-2-hydroxy-propyl)-2-hydroxy-acetamide, and
N-((2S)-3-{2-ethyl-4-[5-(4-isopropoxy-3-methyl-phenyl)-[1,3,4]oxadiazol-2-yl]-6-methyl-phenoxy}-2-hydroxy-propyl)-2-hydroxy-acetamide,
and salts of these compounds.

The compounds of Formula (I) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

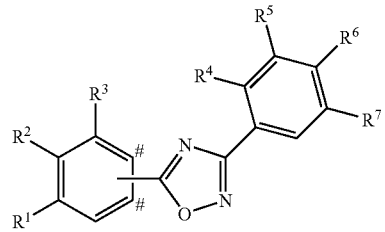

Structure 1

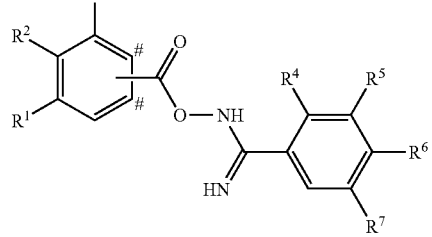

Structure 2

Compounds of Formula (I) which represent a [1,2,4]oxadiazole derivative of Structure 1 are prepared by reacting a compound of Structure 2 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, methoxycarbonylsulfamoyl triethylammonium hydroxide (Burgess reagent), etc.) (Lit.: e.g. C. T. Brain, J. M. Paul, Y. Loong, P. J. Oakley, *Tetrahedron Lett.* 40 (1999) 3275-3278; A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

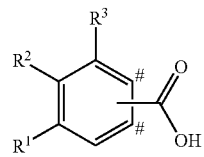

Structure 3

Structure 4

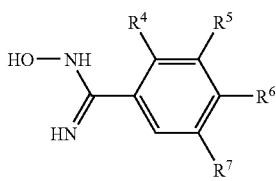

Compounds of Structure 2 may be prepared by reacting a compound of Structure 3 with a compound of Structure 4 in a solvent such as DMF, THF, DCM, etc. in the presence or absence of one or more coupling agents such as TBTU, DCC, EDC, HBTU, PyBOP, CDI, etc. and in the presence or absence of a base such as triethylamine, Hünig's base, NaH, $K_2CO_3$, etc.

Structure 5

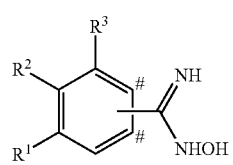

Structure 6

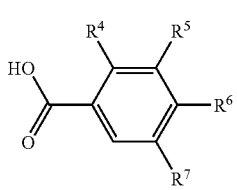

Analogously, cyclizing the hydroxyamidine ester intermediate which is formed upon reacting a hydroxyamidine of Structure 5 with a benzoic acid of Structure 6 gives access to the [1,2,4]oxadiazole derivatives of Structure 7.

Structure 7

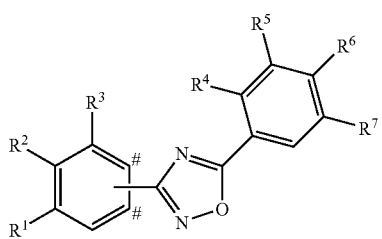

Compounds of Structure 4 and 5 may be prepared by reacting a compound of Structure 9 and 8, respectively, with hydroxylamine or one of its salts in a solvent such as methanol, ethanol, pyridine, etc. in the presence or absence of a base such as $Na_2CO_3$, $K_2CO_3$, potassium tert.-butylate, triethylamine, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

Structure 8

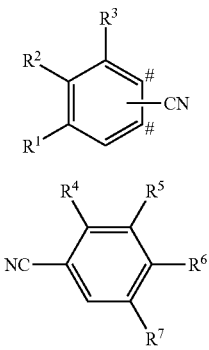

Structure 9

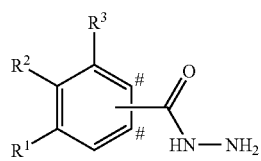

Depending on the nature of the functionalities present in the residues $R^4$ to $R^7$ in Structures 1, 2, 4, 6, 7, and 9, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, $3^{rd}$ Edition, Wiley New York, 1991; P. J. Kocienski, Protecting Groups, Thieme Stuttgart, 1994). Alternatively, the desired residues $R^4$ to $R^7$, in particular $R^6$, may also be introduced in later steps that follow the coupling of the phenyl compounds of Structure 4 and 6 with the phenyl derivatives of Structure 3 and 5, respectively, by using a suitable precursor of a compound of Structure 4 and 6. The phenyl compounds of Structure 4, 6 and 9 or their precursors are either commercially available or are prepared according to procedures known to a person skilled in the art.

Structure 10

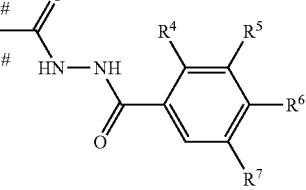

Structure 11

Compounds of Formula (I) which represent a [1,3,4]oxadiazole or a [1,3,4]thiadiazole derivative are prepared similarly by reacting a compound of Structure 3 with hydrazine (by using a coupling reagent such as TBTU, DCC, EDC, HBTU, PyBOP, HOBt, CDI, etc.) to form a compound of Structure 10 which is then coupled with a compound of Structure 6 to give a compound of Structure 11. A compound of Structure 11 can also be prepared by following the reverse reaction order i.e. by first coupling a compound of Structure 6 with hydrazine followed by reacting the corresponding hydrazide intermediate with a compound of Structure 3. Dehydration to the desired [1,3,4]oxadiazole derivative is affected by treating the compound of Structure 11 with a reagent such as POCl$_3$, CCl$_4$ or CBr$_4$ in combination with triphenylphosphine, P$_2$O$_5$, Burgess reagent, etc. in a solvent such as toluene, acetonitrile, dioxane, THF, CHCl$_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278). Likewise, [1,3,4]thiadiazole derivatives are obtained by cyclizing a compound of Structure 11 with Lawesson's reagent optionally in combination with P$_2$S$_5$ in the presence or absence of a solvent such as pyridine, toluene, THF, acetonitrile, etc. at elevated temperatures with or without microwave irradiation (Lit.: e.g. A. A. Kiryanov, P. Sampson, A. J. Seed, *J. Org. Chem.* 66 (2001) 7925-7929).

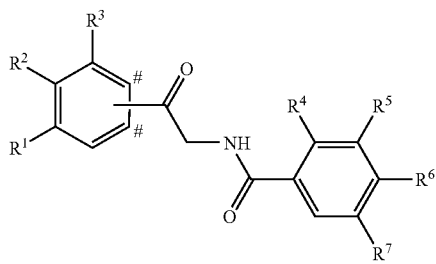

Structure 12

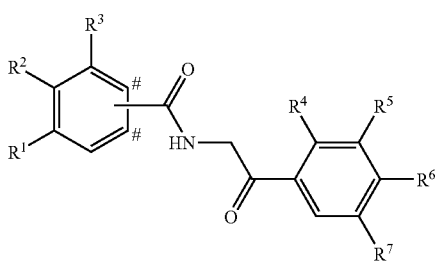

Structure 13

Compounds of Formula (I) which represent an oxazole or a thiazole derivative are prepared by treating a compound of Structure 12 or 13 either with POCl$_3$, PCl$_5$, I$_2$ in combination with triphenylphosphine and triethylamine, Burgess reagent, trifluoracetic anhydride, etc. in a solvent such as toluene, benzene, dioxane, THF, etc. at temperatures between 20 and 120° C., or with Lawesson's reagent, optionally in combination with P$_2$S$_5$, in the presence or absence of a solvent such as pyridine, toluene, THF, acetonitrile, etc. at elevated temperatures with or without microwave irradiation as mentioned above (Lit.: e.g. N. Sato, T. Shibata, M. Jitsuoka, T. Ohno, T. Takahashi, T. Hirohashi, T. Kanno, H. Iwaasa, A. Kanatani, T. Fukami, Takehiro, *Bioorg. & Med. Chem. Lett.* 14 (2004) 1761-1764). The compounds of Structure 12 and 13 are prepared by reacting a compound of Structure 14 and 15 with a compound of Structure 6 and 3, respectively.

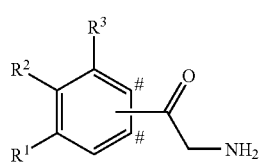

Structure 14

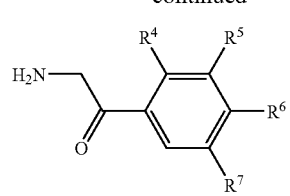

Structure 15

The aminoketons of Structure 14 and 15 can be prepared following literature procedures (e.g. R. A. Glennon, M. L. Bondarev, N. Khorana, R. Young, J. A. May, M. R. Hellberg, M. A. McLaughlin, N. A. Sharif, *J. Med. Chem.* 47 (2004) 6034-6041).

Alternatively, the bond between the either of the two phenyl rings and the central 5-membered heteroaromatic ring can also be formed by applying palladium catalysed cross coupling reactions.

The compounds of Structure 3, 5 and 8 can be prepared following literature procedures (e.g. employing palladium catalysed Suzuki, Heck, or Stille coupling reactions, Friedel Crafts alkylation, Grignard-type alkylation, phenol alkylation reaction, addition of electrophiles to phenyl lithium derivatives, etc.) in one or more steps from commercially available precursors. Methods that effect the transformation of a compound of Structure 3 into a compound of Structure 8, or the opposite, are known to a person skilled in the art.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), t$_R$ is given in min; by TLC (TLC-plates from Merck, Silica gel 60 F$_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

ABBREVIATIONS

As Used Herein

| | |
|---|---|
| aq. | aqueous |
| BSA | bovine serum albumin |
| Bu | butyl |
| CC | column chromatography |
| CDI | carbonyl diimidazole |
| DCC | dicyclohexyl carbodiimide |
| DCM | dichloromethane |
| DIPEA | diisopropyl-ethylamine, Hünig's base, ethyl-diisopropylamine |
| DMF | dimethylformamide |
| DMSO | dimethylsulfoxide |

| | |
|---|---|
| EA | ethyl acetate |
| EDC | N-(3-dimethylaminopropyl)-N'-ethyl-carbodiimide |
| EtOH | ethanol |
| h | hour(s) |
| HBTU | O-(benzotriazol-1-yl)-N,N,N',N'-tetramethyluronium hexafluorophosphate |
| HOBt | 1-hydroxybenzotriazole |
| HPLC | high performance liquid chromatography |
| HV | high vacuum conditions |
| LC-MS | liquid chromatography-mass spectrometry |
| Lit. | literature |
| min | minute(s) |
| MPLC | medium pressure liquid chromatography |
| NaOAc | sodium acetate |
| NMO | N-methyl-morpholine-N-oxide |
| org. | organic |
| prep. | Preparative |
| PyBOP | benzotriazol-1-yl-oxy-tris-pyrrolidino-phosphonium-hexafluoro-phosphate |
| rt | room temperature |
| sat. | saturated |
| S1P | sphingosine 1-phosphate |
| TBTU | 2-(1H-benzotriazole-1-yl)-1,2,3,3-tetramethyluronium tetrafluoroborate |
| TFA | trifluoroacetic acid |
| THF | tetrahydrofuran |
| TLC | thin layer chromatography |
| $t_R$ | retention time |

4-Isopropoxy-benzoic acid

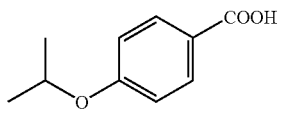

4-Isopropoxy-benzoic acid is commercially available.

4-Isopropoxy-3-methyl-benzoic acid

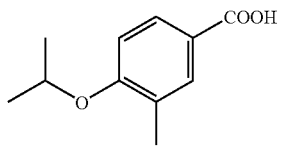

To a solution of 4-hydroxy-3-methyl-benzoic acid (2.00 g, 13.15 mmol) in DMF (50 mL), K$_2$CO$_3$ (8.17 g, 59.15 mmol) followed by 2-iodopropane (6.70 g, 39.44 mmol) is added. The suspension is refluxed for 20 h. The mixture is filtered and the solvent of the filtrate is evaporated. The residue is dissolved in EA and washed with water. The org. extract is concentrated and then separated by CC on silica gel eluting with heptane:EA 5:1 to give isopropyl 4-isopropoxy-3-methyl-benzoate which is dissolved in methanol (50 mL) and 2 N aq. LiOH solution (10 mL). The mixture is stirred at 80° C. for 5 h before it is acidified with 1 N aq. HCl, diluted with water and extracted with EA. The org. extract is washed with water and concentrated. The crystalline product is dried under HV to give 4-isopropoxy-3-methyl-benzoic acid (1.77 g) as white crystals; LC-MS: $t_R$=0.90 min, [M+1]$^+$=195.14.

4-Isopropoxy-3,5-dimethyl-benzoic acid

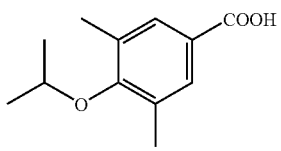

A mixture of 4-bromo-2,6-dimethylphenol (4.69 g, 23.3 mmol), 2-iodo-propane (15.81 g, 93.0 mmol) in isopropanol (200 mL) and 1 N aq. NaOH (50 mL) is stirred at rt for 24 h. The mixture is diluted with diethyl ether, washed with 1 N aq. HCl and 1 N aq. NaOH, dried over Na$_2$SO$_4$, filtered and concentrated to give crude 5-bromo-2-isopropoxy-1,3-dimethyl-benzene (4.62 g) as an orange oil; LC-MS: $t_R$=1.07 min. The arylbromide is dissolved in THF (100 mL) and cooled to −78° C. BuLi (15 mL of a 1.6 N solution in hexane) is slowly added (30 min) and the mixture is stirred at −78° C. for 30 min. The mixture is transferred via needle to a cooled (0° C.) solution of dimethylcarbonate (10.7 g, 118.8 mmol) in THF (50 mL). The mixture is stirred for 15 h, quenched with 3 N aq. LiOH (100 mL) and stirred at 60° C. for 24 h. The mixture is diluted with ether (200 mL) and 1M aq. NaOH (100 mL), the phases separated and the org. phase re-extracted with NaOH (50 mL). The aq. phases are washed with diethyl ether (2×50 mL), carefully acidified to pH 3 with 25% HCl. The org. phases are discarded. The aq. phase is extracted with DCM (5×75 mL). The org. extracts are dried over Na$_2$SO$_4$, filtered and evaporated to give 4-isopropoxy-3,5-dimethyl-benzoic acid (2.23 g) as a beige solid; LC-MS: $t_R$=0.91 min, [M+1]$^+$=209.07, $^1$H NMR (CDCl$_3$): δ 1.34 (d, J=6.3 Hz, 6H), 2.34 (s, 6H), 4.32 (hept, J=6.0 Hz, 1H), 7.81 (s, 2H).

3-Isopropoxy-4-methyl-benzoic acid

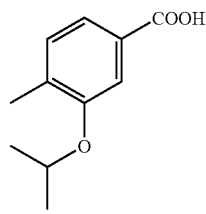

3-Isopropoxy-4-methyl-benzoic acid (1.70 g) is prepared in analogy to 4-isopropoxy-3-methyl-benzoic acid starting from 3-hydroxy-4-methyl-benzoic acid (2.00 g); LC-MS: $t_R$=0.91 min.

4-Isobutyl-benzoic acid

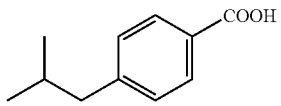

4-Isobutyl-benzoic acid is commercially available.

4-Isobutyl-3-methyl-benzoic acid

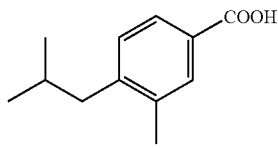

A mixture of methyl 4-bromo-3-methylbenzoate (9.47 g, 39.3 mmol), 2-methylpropyl boronic acid (2.0 g, 9.62 mmol), $K_2CO_3$ (8.13 g, 58.9 mmol) and $Ag_2O$ (10.9 g, 47.1 mmol) in dioxane (150 mL) is degassed and set under an $N_2$-atmosphere before 1,1-bis(diphenylphosphino)ferrocene-palladium(II)dichloride dichloromethane complex (808 mg, 0.99 mmol) is added. The mixture is stirred at 75° C. for 24 h. Another portion of 1,1'-bis(diphenylphosphino)ferrocene-palladium(II)dichloride dichloromethane complex (808 mg, 0.99 mmol) is added and stirring is continued at 75° C. for 20 h. The mixture is filtered over Celite and the solvent of the filtrate is evaporated. The cured product is purified by prep. HPLC to give methyl 4-isobutyl-3-methyl benzoate (1.65 g) as a colourless oil. This oil is dissolved in methanol (50 mL) and 2 N LiOH (10 mL) and stirred at rt for 20 h. The mixture is acidified with aq. HCl and extracted twice with EA. The combined org. extracts are dried over $MgSO_4$, filtered and evaporated to give 4-isobutyl-3-methyl-benzoic acid (1.65 g) as white crystals; LC-MS: $t_R$=0.93 min, $[M+1+CH_3CN]^+$= 234.16, $^1$H NMR (CDCl$_3$): δ 0.87 (d, J=6.4 Hz, 6H), 1.75-1.91 (m, 1H), 2.29 (s, 3H), 2.47 (d, J=7.3 Hz, 2H), 7.12 (d, J=7.6 Hz, 1H), 7.79 (d, J=7.9 Hz, 1H), 7.82 (s, 1H).

3-Isobutyl-benzoic acid

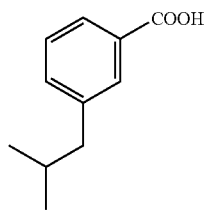

In an oven-dried round bottom flask Mg turnings (1.13 g, 46.6 mmol) are suspended in THF (1 mL). 1-Bromo-3-methylbutane (6.37 g, 46.5 mmol) is carefully added while the mixture is initially heated to reflux. The mixture is stirred for approximately 30 min until the Mg has dissolved. The mixture is then added to a cold (5° C.) solution of $ZnBr_2$ (10.47 g, 46.5 mmol) in THF (80 mL). The thick suspension is stirred at 0° C. for 20 min before it is cooled to −75° C. 1,1'-bis (diphenylphosphino)ferrocene-palladium(II) dichloride dichloromethane complex (184 mg, 0.225 mmol) followed by methyl-3-bromobenzoate (5.0 g, 23.3 mmo) is then added. The mixture is warmed to rt and stirred for 24 h. The reaction mixture is diluted with water and extracted with EA. The org. extract is dried over $MgSO_4$, filtered and evaporated. The crude product is purified by CC on silica gel eluting with heptane:EA 20:1 to give methyl 3-isobutyl-benzoate (4.34 g) as a colourless oil. This material is dissolved in methanol (50 mL) and 2 N aq. LiOH (10 mL) and stirred at rt for 16 h. The mixture is acidified by adding 1 N aq. HCl and extracted with EA. The org. extracts are dried over $MgSO_4$, filtered and evaporated to give 3-isobutyl-benzoic acid (3.84 g) as a colourless oil; LC-MS: $t_R$=0.91 min; $^1$H NMR (CDCl$_3$): δ 0.87 (d, J=6.7 Hz, 6H), 1.77-1.94 (m, 1H), 2.48 (d, J=7.0 Hz, 2H), 7.29-7.35 (m, 2H), 7.86 (s, 1H), 7.88-7.94 (m, 1H).

4,N-Dihydroxy-3,5-dimethyl-benzamidine

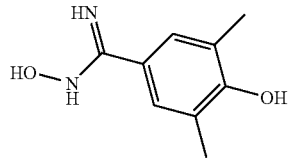

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR (CD$_3$OD): δ 7.20 (s, 2H), 2.20 (s, 6H).

4-Allyloxy-N-hydroxy-3,5-dimethyl-benzamidine

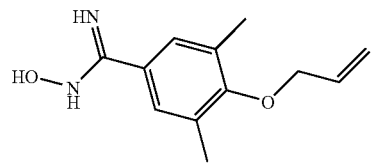

The title compound is prepared by allylating commercially available 4-hydroxy-3,5-dimethyl-benzonitrile with allylbromide in the presence of NaOH in isopropanol at rt. The nitrile is then transformed to the hydroxyamidine according to literature procedures (e.g. E. Meyer, A. C. Joussef, H. Gallardo, *Synthesis* 2003, 899-905); $^1$H NMR (CD$_3$OD): δ 7.27 (s, 2H), 6.10 (m, 1H), 5.42 (m, 1H), 5.26 (m, 1H), 4.31 (dt, J=5.6, 1.5 Hz, 2H), 2.29 (s, 6H).

3-Ethyl-4,N-dihydroxy-5-methyl-benzamidine

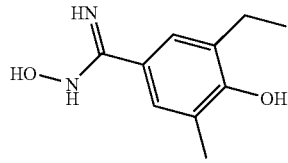

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-

DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4-Allyloxy-3-ethyl-N-hydroxy-5-methyl-benzamidine

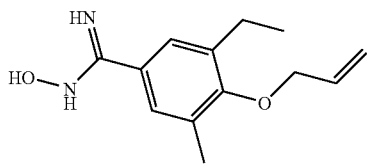

The title compound is prepared by allylating 3-ethyl-4-hydroxy-5-methyl-benzaldehyde which is prepared from 2-ethyl-6-methyl-phenol following literature procedures (see 3-ethyl-4,N-dihydroxy-5-methyl-benzamidine). The aldehyde is then transformed into the corresponding hydroxyamidine according to literature procedures (see 3-ethyl-4,N-dihydroxy-5-methyl-benzamidine); LC-MS: $t_R$=0.72 min, [M+1]$^+$=235.09, $^1$H NMR (CD$_3$OD): δ 7.31 (s, 1H), 7.29 (s, 1H), 6.10 (m, 1H), 5.43 (dd, J=17.0, 1.5 Hz, 1H), 5.27 (dd, J=10.3, 1.2 Hz, 1H), 4.81 (s br, 3H), 4.31 (d, J=5.6 Hz, 2H), 2.67 (q, J=7.6 Hz, 2H), 2.30 (s, 3H), 1.23 (t, J=7.6 Hz, 4H).

3,5-Diethyl-4,N-dihydroxy-benzamidine

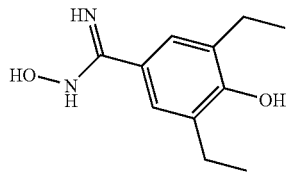

The title compound is prepared from commercially available 2,6-diethylaniline following literature procedures (G. G. Ecke, J. P. Napolitano, A. H. Filbey, A. J. Kolka, *J. Org. Chem.* 22 (1957) 639-642; and literature cited for 3-ethyl-4,N-dihydroxy-5-methyl-benzamidine).

4-Allyloxy-N-hydroxy-2-methoxy-benzamidine

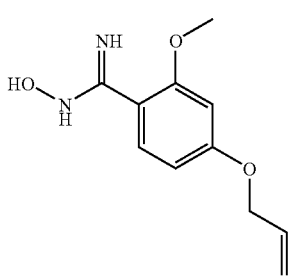

The title compound is prepared from commercially available 4-hydroxy-2-methoxy-benzaldehyde following literature procedures (references cited for 3-ethyl-4,N-dihydroxy-5-methyl-benzamidine); LC-MS: $t_R$=0.64 min, [M+1]$^+$=223.24, $^1$H NMR (D$_6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

4-Allyloxy-3,5-dimethyl-benzoic acid hydrazide

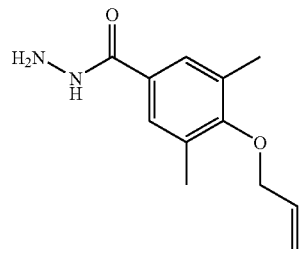

a) A mixture of 4-bromo-2,6-dimethyl-phenol (20.1 g, 100 mmol) and allylchloride (32.7 g, 428 mmol) in 3 N aq. NaOH (100 mL) and isopropanol (250 mL) is stirred at 60° C. for 15 h before it is diluted with 1 N aq. NaOH (100 mL). The mixture is extracted with diethyl ether (300 mL, 150 mL) and the combined org. extracts are washed with 1 N aq. NaOH (2×100 mL), 1 M aq. NaH$_2$PO$_4$ (50 mL), dried over Na$_2$SO$_4$, filtered and concentrated to give 2-allyloxy-5-bromo-1,3-dimethyl-benzene (23.6 g) as a yellow oil, LC-MS: $t_R$=1.08 min, [M+1]$^+$=241.20.

b) To a solution of 2-allyloxy-5-bromo-1,3-dimethyl-benzene (23.6 g, 98.0 mmol) in THF (150 mL) is added at −75° C. a solution of n-BuLi (90 mL, 1.5 M in diethyl ether). The temperature remains at −75° C. The mixture is stirred for 30 min and then transferred via double-tip canula into a cooled (0° C.) solution of dimethylcarbonate (21.4 g, 238 mmol) in THF (90 mL). The mixture is stirred for 2 h at 0° C., then warmed to rt during 15 h. The solvent of the mixture is evaporated and re-evaporated with EtOH (200 mL) to remove most of the butylacetate side product. The mixture is taken up in 2 N aq. LiOH (150 mL) and EtOH (200 mL) and stirred at rt for 2 h then at 60° C. for 1 h. The EtOH is evaporated and the remaining mixture is diluted with 0.5 N aq. NaOH and extracted with diethyl ether (200 mL). The org. extract is washed with 1M aq. NaOH (5×50 mL) and the combined aq. washings are re-extracted with ether (100 mL). The aq. phase is acidified with 25% aq. HCl and extracted with DCM (5×50 mL). The combined org. extracts are dried over Na$_2$SO$_4$, filtered, evaporated and dried in vacuo at 60° C. for 15 h to give 4-allyloxy-3,5-dimethyl-benzoic acid (8.0) as a yellow-brown solid. LC-MS: $t_R$=0.90 min.

c) To a solution of 4-allyloxy-3,5-dimethyl-benzoic acid (5.26 g, 25.5 mmol) in CHCl$_3$ (75 mL), thionylchloride (7.5 mL, 103 mmol) is added at rt. The mixture is refluxed for 2 h before the solvent is evaporated to give crude 4-allyloxy-3,5-dimethyl-benzoic acid chloride as a brownish oil. To a solution of the acid chloride in DCM (50 mL) hydrazine (75 mL of a 1 M solution in THF) in DCM (250 mL) is added at 0° C. The mixture is stirred at rt for 15 h before it is diluted with diethyl ether and extracted with 1 N aq. HCl (75 mL, then 5×50 mL). The combined aq. extracts are basified by adding 33% aq. KOH solution and extracted with DCM (5×50 mL). The combined DCM extracts are dried over Na$_2$SO$_4$, filtered and evaporated to give 4-allyloxy-3,5-dimethyl-benzoic acid hydrazide (5.39 g) as a white solid; LC-MS: $t_R$=0.71 min, [M+1]$^+$=221.20, $^1$H NMR (D$_6$-DMSO): δ 2.22 (s, 6H), 4.28-4.37 (m, 2H), 4.39 (s, 2H), 5.19-5.28 (m, 1H), 5.36-5.47 (m, 1H), 6.00-6.15 (m, 1H), 7.49 (s, 2H), 9.55 (s, 1H).

4-Benzyloxy-3-ethyl-5-methyl-benzoic acid hydrazide

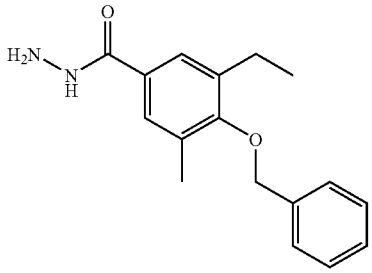

a) 3-Ethyl-4-hydroxy-5-methyl-benzaldehyde is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

b) To a solution of 3-ethyl-4-hydroxy-5-methyl-benzaldehyde (8.00 g, 48.7 mmol) in acetone (130 mL), K$_2$CO$_3$ (20.2 g, 146.2 mmol) followed by benzylbromide (12.5 g, 73.1 mmol) is added. The suspension is stirred at reflux for 16 h before it is filtered and the solvent of the filtrate is removed in vacuo. The residue is separated by CC on silica gel to give 4-benzyloxy-3-ethyl-5-methyl-benzaldehyde (9.07 g) as a pale yellow oil; LC-MS: $t_R$=1.09 min, [M+1]$^+$=255.08.

c) To a solution of 4-benzyloxy-3-ethyl-5-methyl-benzaldehyde (5.6 g, 22.0 mmol) in acetone (150 mL), KMnO$_4$ (4.52 g, 28.6 mmol) is added. The mixture becomes slightly warm (45° C.) and is stirred for 90 min at rt. The mixture is filtered and the filtrate is evaporated. The residue is treated with water and 10% aq. citric acid solution and extracted twice with EA. The combined org. extracts are dried over MgSO$_4$, filtered, concentrated and dried under HV to give 4-benzyloxy-3-ethyl-5-methylbenzoic acid (4.38 g) as a white solid; LC-MS: $t_R$=1.00 min, [M+1+CH$_3$CN]$^+$=312.09.

d) To a solution of 4-benzyloxy-3-ethyl-5-methylbenzoic acid (4.38 g, 17.2 mmol) in chloroform (60 mL), thionylchloride (5 mL, 68.9 mmol) is added. The mixture is refluxed for 2.5 h before the solvent is evaporated in vacuo. The remaining red oil is dissolved in THF (150 mL) and then added dropwise to a solution of hydrazine hydrate (3.46 g, 69.3 mmol) in THF (80 mL). The mixture is stirred 2 h at rt, diluted with diethyl ether, washed with 1 N aq. HCl, dried over MgSO$_4$, filtered, concentrated and dried to give 4-benzyloxy-3-ethyl-5-methyl-benzoic acid hydrazide (1.16 g) as a white solid; LC-MS: $t_R$=0.82 min, [M+1]$^+$=285.47, $^1$H NMR (CDCl$_3$): δ 0.98 (t, J=7.3 Hz, 3H), 1.98 (s, 3H), 2.39 (q, J=7.3 Hz, 2H), 4.49 (s, 2H), 7.20-7.32 (m, 5H) 7.57 (s, 1H), 7.65 (s, 1H), 11.23 (s, 1H).

Methanesulfonic acid 2,2-dimethyl-[1,3]dioxan-5-ylmethyl ester

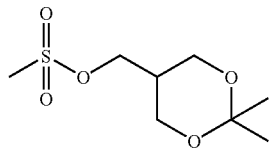

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

Example 1

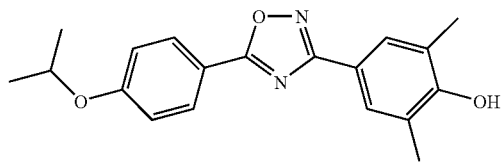

a) To a solution of 4,N-dihydroxy-3,5-dimethyl-benzamidine (2.29 g, 8.88 mmol) and 4-isopropoxy benzoic acid (2.00 g, 11.1 mmol) in DMF (50 mL), TBTU (4.64 g, 14.4 mmol) and DIPEA (5.02 g, 38.8 mmol) is added. The mixture is stirred at rt for 16 h before the solvent is removed in vacuo. The residue is diluted with EA, washed with water, dried over MgSO$_4$, filtered and concentrated. The crude product is purified by CC on silica gel eluting with heptane:EA 4:1 to 1:1 to give 4-isopropoxy-benzoic acid (4,N-dihydroxy-3,5-dimethyl-benzamidine) ester (1.36 g) as an orange solid; LC-MS: $t_R$=0.93 min, [M+1]$^+$=343.19.

b) A solution of 4-isopropoxy-benzoic acid (4,N-dihydroxy-3,5-dimethyl-benzamidine) ester (1.36 g, 3.97 mmol) in acetonitrile (25 mL) and toluene (25 mL) is stirred at 90° C. for 72 h. The solvent is evaporated and the crude product is purified by CC on silica gel eluting with heptane:EA 17:3 to give 4-[5-(4-isopropoxy-phenyl)-[1,2,4]oxadiazol-3-yl]-2,6-dimethyl-phenol (380 mg) as a brownish crystalline solid; LC-MS: $t_R$=1.08 min, [M+1]$^+$=325.13, $^1$H NMR (CDCl$_3$): δ 8.14 (d, J=5.9 Hz, 2H), 7.81 (s, 2H), 7.00 (d, J=5.6 Hz, 2H), 4.91 (s br, 1H), 4.72-4.62 (m, 1H), 2.32 (s, 6H), 1.39 (s, 6H).

Example 2

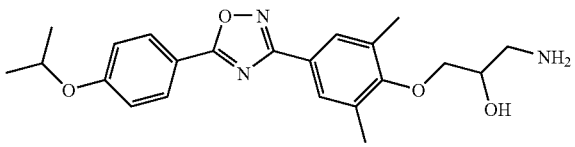

a) A mixture of 4-[5-(4-isopropoxy-phenyl)-[1,2,4]oxadiazol-3-yl]-2,6-dimethyl-phenol (370 mg, 1.14 mmol) and epichlorohydrine (317 mg, 3.42 mmol) in isopropanol (5 mL) and 3 N aq. NaOH (1.5 mL) is stirred at rt for 16 h. The mixture is diluted with EA, washed with water, dried over MgSO$_4$, filtered and concentrated. The crude product is purified by chromatography on prep. TLC plates with heptane:EA 3:1 to give 3-(3,5-dimethyl-4-oxiranylmethoxy-phenyl)-5-(4-isopropoxy-phenyl)-[1,2,4]oxadiazole (256 mg) as white solid; LC-MS: t$_R$=1.14 min, [M+1]$^+$=381.18.

b) A solution of 3-(3,5-dimethyl-4-oxiranylmethoxy-phenyl)-5-(4-isopropoxy-phenyl)-[1,2,4]oxadiazole (250 mg, 0.657 mmol) in 7 N NH$_3$ in methanol (10 mL) is stirred at 60° C. for 16 h. The solvent is evaporated and the remaining residue is dried under HV to give 1-amino-3-{4-[5-(4-isopropoxy-phenyl)-[1,2,4]oxadiazol-3-yl]-2,6-dimethyl-phenoxy}-propan-2-ol (278 mg) as a beige oil; LC-MS: t$_R$=0.86 min, [M+1]$^+$=398.44.

Example 3

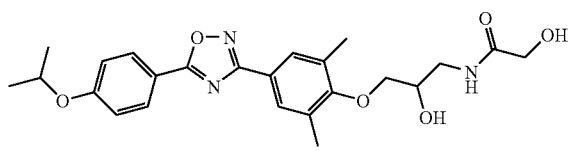

A solution of 1-amino-3-{4-[5-(4-isopropoxy-phenyl)-[1,2,4]oxadiazol-3-yl]-2,6-dimethyl-phenoxy}-propan-2-ol (277 mg, 0.698 mmol), glycolic acid (80 mg, 1.05 mmol), DIPEA (362 mg, 2.80 mmol) and TBTU (382 mg, 1.19 mmol) in DMF (10 mL) is stirred at rt for 16 h before it is diluted with EA, washed with water, and concentrated. The crude product is purified by chromatography on prep. TLC plates with DCM containing 10% of methanol to give 2-hydroxy-N-(2-hydroxy-3-{4-[5-(4-isopropoxy-phenyl)-[1,2,4]oxadiazol-3-yl]-2,6-dimethyl-phenoxy}-propyl)-acetamide (64 mg) as a pale yellow solid, LC-MS: t$_R$=0.94 min, [M+1]$^+$=456.18, $^1$H NMR (D$_6$-DMSO): δ 1.30 (d, J=5.9 Hz, 6H), 2.31 (s, 6H), 3.16-3.25 (m, 2H), 3.63-3.79 (m, 2H), 3.81 (d, J=5.6 Hz, 2H), 3.86-3.97 (m, 1H), 4.72-4.83 (m, 1H), 5.28 (d, J=5.3 Hz, 1H), 5.54 (t, J=5.9 Hz, 1H), 7.14 (d, J=9.1 Hz, 2H), 7.68 (t, J=5.6 Hz, 1H), 7.73 (s, 2H), 8.08 (d, J=9.1 Hz, 2H).

Examples 4 to 9

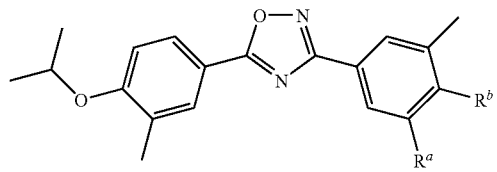

The following examples are prepared in analogy to previous examples starting from 4-isopropoxy-3-methyl-benzoic acid and either 4,N-dihydroxy-3,5-dimethyl-benzamidine (Examples 4 to 6) or 4,N-dihydroxy-3-ethyl-5-methyl-benzamidine (Examples 7 to 9):

| Example | prepared in analogy to Example | R$^a$ | R$^b$ | LC-MS t$_R$ (min) | [M + H]$^+$ |
|---|---|---|---|---|---|
| 4 | 1 | CH$_3$ | OH | 1.15 | 339.12 |
| 5 | 2 | CH$_3$ | -CH2-NH2) | 0.89 | 412.21 |
| 6 | 3 | CH$_3$ | -CH2-NH-CO-CH2-OH) | 1.02 | 470.21 |
| 7 | 1 | CH$_2$CH$_3$ | OH | 1.14 | 353.50 |
| 8 | 2 | CH$_2$CH$_3$ | -CH2-NH2) | 0.88 | 426.62 |
| 9 | 3 | CH$_2$CH$_3$ | -CH2-NH-CO-CH2-OH) | 1.04 | 484.24 |

Example 6

$^1$H NMR (D$_6$-DMSO): δ 1.31 (d, J=6.2 Hz, 6H), 2.21 (s, 3H), 2.31 (s, 6H), 3.13-3.26 (m, 1H), 3.36-3.47 (m, 1H), 3.65-3.78 (m, 2H), 3.81 (d, J=5.3 Hz, 2H), 3.86-3.99 (m, 1H), 4.69-4.82 (m, 1H), 5.28 (d, J=5.0 Hz, 1H), 5.54 (t, J=5.9 Hz, 1H), 7.18 (d, J=9.4 Hz, 1H), 7.68 (t, J=5.9 Hz, 1H), 7.73 (s, 2H), 7.94-7.99 (m, 2H).

Example 9

$^1$H NMR (D$_6$-DMSO): δ 1.20 (t, J=7.3 Hz, 3H), 1.32 (d, J=6.2 Hz, 6H), 2.21 (s, 3H), 2.32 (s, 3H), 2.70 (q, J=7.6 Hz, 2H), 3.14-3.25 (m, 1H), 3.37-3.46 (m, 1H), 3.68-3.77 (m, 2H), 3.81 (d, J=5.6 Hz, 2H), 3.89-3.98 (m, 1H), 4.69-4.81 (m, 1H), 5.27 (d, J=5.3 Hz, 1H), 5.52 (t, J=5.6 Hz, 1H), 7.18 (d, J=9.4 Hz, 1H), 7.66 (t br, J=5.9 Hz, 1H), 7.74 (s, 2H), 7.93-8.00 (m, 2H).

Example 10

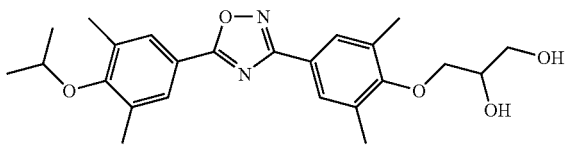

a) To a mixture of 4-isopropoxy-3,5-dimethyl-benzoic acid (175 mg, 794 µmol), 4-allyloxy-N-hydroxy-3,5-dimethyl-benzamidine (165 mg, 792 µmol) and DIPEA (128 mg, 993 µmol) in DCM (10 mL), TBTU (321 mg, 1.00 mmol) is added at 0° C. The mixture is stirred at 0° C. for 1 h, then at rt for 5 h, before it is diluted with EA (100 mL) and washed with sat. aq. NaHCO$_3$ solution (2×30 mL). The org. extract is dried over Na$_2$SO$_4$, filtered and evaporated. The residue is dissolved in dioxane (10 mL) and stirred at 90° C. for 2 days. The solvent is evaporated and the residue is dried to give crude 3-(4-allyloxy-3,5-dimethyl-phenyl)-5-(4-isopropoxy-3,5-dimethyl-phenyl)-[1,2,4]oxadiazole (346 mg); LC-MS: $t_R$=1.25 min, [M+1]$^+$=393.47.

b) To a solution of the crude 3-(4-allyloxy-3,5-dimethyl-phenyl)-5-(4-isopropoxy-3,5-dimethyl-phenyl)-[1,2,4]oxadiazole (346 mg, 0.794 mmol) in a mixture of acetone (10 mL) and water (1 mL), NMO (535 mg, 3.96 mmol) and OsO$_4$ (36 mg, 4 µmol, 2.5% solution in butanol) is added. The mixture is stirred at rt for 2 days before it is diluted with water (50 mL) and extracted with EA (100 mL, 2×50 mL). The combined org. extracts are dried over Na$_2$SO$_4$, filtered and concentrated. The crude product is purified by CC on silica gel eluting with EA to give 3-{4-[5-(4-isopropoxy-3,5-dimethyl-phenyl)-[1,2,4]oxadiazol-3-yl]-2,6-dimethyl-phenoxy}-propane-1,2-diol (175 mg) as a colourless oil which slowly solidifies; LC-MS: $t_R$=1.07 min, [M+1]$^+$=427.19, $^1$H NMR (D$_6$-DMSO): δ 1.27 (d, J=6.3 Hz, 6H), 2.31 (s, 6H), 2.33 (s, 6H), 3.51 (t, J=5.5 Hz, 2H), 3.71-3.78 (m, 1H), 3.80-3.89 (m, 2H), 4.31 (hept, J=6.0 Hz), 4.64 (t, J=5.5 Hz, 1H), 4.96 (d, J=5.3 Hz, 1H), 7.74 (s, 2H), 7.84 (s, 2H).

Example 11

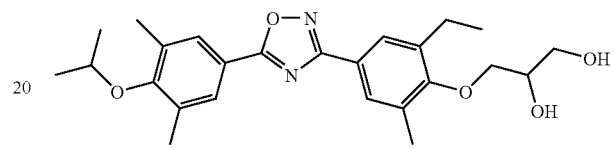

3-{2-Ethyl-4-[5-(4-isopropoxy-3,5-dimethyl-phenyl)-[1,2,4]oxadiazol-3-yl]-6-methyl-phenoxy}-propane-1,2-diol is prepared in analogy to Example 10 starting from 4-isopropoxy-3,5-dimethyl-benzoic acid and 4-allyloxy-3-ethyl-N-hydroxy-5-methyl-benzamidine; LC-MS: $t_R$=1.09 min, [M+1]$^+$=441.25.

Examples 12 to 23

The following examples are prepared in analogy to previous examples starting from 4,N-dihydroxy-3,5-dimethyl-benzamidine and either 3-isopropoxy-4-methyl-benzoic acid (Examples 12 to 14), 4-isobutylbenzoic acid (Examples 15 to 17), 4-isobutyl-3-methyl-benzoic acid (Examples 18 to 20), or 3-isobutylbenzoic acid (Examples 21 to 23):

| Example | prepared in analogy to Example | R$^a$ | R$^b$ | R$^c$ | LC-MS $t_R$ (min) | [M + H]$^+$ |
|---|---|---|---|---|---|---|
| 12 | 1 | methyl | iso-propoxy | OH | 1.15 | 339.07 |
| 13 | 2 | methyl | iso-propoxy | -CH2-NH2) | 0.89 | 412.24 |

-continued

| Example | prepared in analogy to Example | $R^a$ | $R^b$ | $R^c$ | LC-MS $t_R$ (min) | $[M+H]^+$ |
|---|---|---|---|---|---|---|
| 14 | 3 | methyl | iso-propoxy | (structure) | 1.02 | 470.17 |
| 15 | 1 | isobutyl | H | OH | 1.17 | 323.21 |
| 16 | 2 | isobutyl | H | (structure) | 0.91 | 396.33 |
| 17 | 3 | isobutyl | H | (structure) | 1.03 | 454.45 |
| 18 | 1 | isobutyl | methyl | OH | 1.18 | 337.23 |
| 19 | 2 | isobutyl | methyl | (structure) | 0.93 | 410.06 |
| 20 | 3 | isobutyl | methyl | (structure) | 1.06 | 468.21 |
| 21 | 1 | H | isobutyl | OH | 1.13 | 323.14 |
| 22 | 2 | H | isobutyl | (structure) | 0.88 | 396.23 |
| 23 | 3 | H | isobutyl | (structure) | 1.00 | 454.18 |

Example 12

$^1$H NMR (CDCl$_3$: δ 1.40 (d, J=6.2 Hz, 6H), 2.28 (s, 3H), 2.33 (s, 6H), 4.71 (hept, J=5.9 Hz, 1H), 4.98 (s, 1H), 7.28 (d, J=7.6 Hz, 1H), 7.63 (d, J=1.5 Hz, 1H), 7.69 (dd, J=7.9, 1.5 Hz, 1H), 7.82 (s, 2H).

Example 15

$^1$H NMR (D$_6$-DSMO): δ 0.87 (d, J=6.4 Hz, 6H), 1.82-1.96 (m, 1H), 2.24 (s, 6H), 2.55 (d, J=7.3 Hz, 2H), 7.42 (d, J=8.2 Hz, 2H), 7.65 (s, 2H), 8.06 (d, J=8.2 Hz, 2H), 8.95 (s, 1H).

Example 20

$^1$H NMR (CDCl$_3$: δ 0.95 (d, J=6.4 Hz, 6H), 1.82-1.99 (m, 1H), 2.35 (s, 6H), 2.39 (s, 3H), 2.55 (d, J=7.3 Hz, 2H), 3.41-3.57 (m, 2H), 3.71-3.91 (m, 3H), 4.18 (s, 2H), 7.04 (t, J=5.6 Hz, 1H), 7.25 (d, J=7.9 Hz, 1H), 7.83 (s, 2H), 7.93 (d, J=7.9 Hz), 7.97 (s, 1H).

Example 24

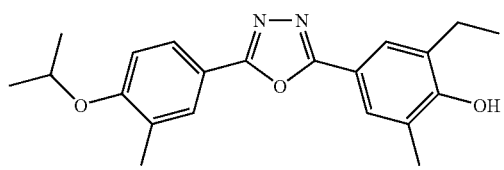

a) To a solution of 4-isopropoxy-3-methyl-benzoic acid (1.35 g, 6.95 mmol) in chloroform (20 mL), thionylchloride (2.48 g, 20.9 mmol) is added. The mixture is refluxed for 2 h before the solvents are removed in vacuo to give crude 4-isopropoxy-3-methyl-benzoic acid chloride; LC-MS: $t_R$=1.00 min.

b) To a suspension of 4-benzyloxy-3-ethyl-5-methyl-benzoic acid hydrazide (1.12 g, 3.95 mmol) in DCM (20 mL), triethylamine (500 mg, 4.94 mmol) is added. The clear solution is cooled to 5° C. before a solution of 4-isopropoxy-3-methyl-benzoic acid chloride (700 mg, 3.29 mmol) in DCM (10 mL) is added dropwise. The suspension is stirred at rt for 1 h before it is diluted with EA, washed with 1 N aq. HCl, followed by water, dried over $MgSO_4$, filtered, concentrated and dried to give 4-benzyloxy-3-ethyl-5-methyl-benzoic acid N'-(4-isopropoxy-3-methyl-benzoyl)-hydrazide (1.57 g) as a white solid; LC-MS: $t_R$=1.05 min, $[M+1]^+$=461.66.

c) A solution of 4-benzyloxy-3-ethyl-5-methyl-benzoic acid N'-(4-isopropoxy-3-methyl-benzoyl)-hydrazide (1.57 g, 3.40 mmol) and Burgess reagent (1.06 g, 4.43 mmol) in THF (30 mL) is heated to 110° C. under microwave irradiation for 3 min. The mixture is cooled, diluted with diethyl ether, washed with water, dried over $MgSO_4$, filtered and concentrated. The crude product is purified by CC on silica gel eluting with heptane:EA 5:1 to give 2-(4-benzyloxy-3-ethyl-5-methyl-phenyl)-5-(4-isopropoxy-3-methyl-phenyl)-[1,3,4]oxadiazole (1.25 g) as a colourless oil; LC-MS: $t_R$=1.24 min, $[M+1]^+$=443.58.

d) To a solution of 2-(4-benzyloxy-3-ethyl-5-methyl-phenyl)-5-(4-isopropoxy-3-methyl-phenyl)-[1,3,4]oxadiazole (1.25 g, 2.82 mmol) in THF (10 mL), Pd/C (100 mg, 10% Pd) in EtOH (10 mL) is added. The mixture is stirred at rt under 1 atmosphere of $H_2$ for 16 h before the catalyst is removed by filtration. The filtrate is concentrated and separated by CC on silica gel eluting with heptane:EA 4:1 to 1:1 to give 2-ethyl-4-[5-(4-isopropoxy-3-methyl-phenyl)-[1,3,4]oxadiazol-2-yl]-6-methyl-phenol (0.79 g) as a greenish solid; LC-MS: $t_R$=1.12 min, $[M+1]^+$=353.17, $^1H$ NMR ($D_6$-DMSO): δ 9.02 (s br, 1H), 7.90-7.86 (m, 2H), 7.70-7.66 (m, 2H), 7.13 (d, J=9.4 Hz, 1H), 4.72 (hept, J=5.0^9 Hz, 1H), 2.65 (q, J=7.6 Hz, 2H), 2.26 (s, 3H), 2.20 (s, 3H), 1.31 (d, J=5.9 Hz, 6H), 1.17 (t, J=7.6 Hz, 3H).

Example 25

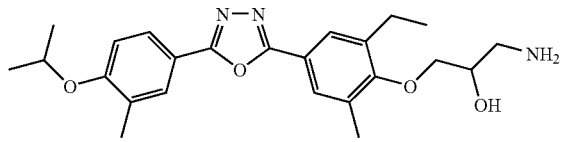

1-Amino-3-{2-ethyl-4-[5-(4-isopropoxy-3-methyl-phenyl)-[1,3,4]oxadiazol-2-yl]-6-methyl-phenoxy}-propan-2-ol is prepared in analogy to Example 2 starting from 2-ethyl-4-[5-(4-isopropoxy-3-methyl-phenyl)-[1,3,4]oxadiazol-2-yl]-6-methyl-phenol; LC-MS: $t_R$=0.84 min, $[M+1]^+$=426.45.

Example 26

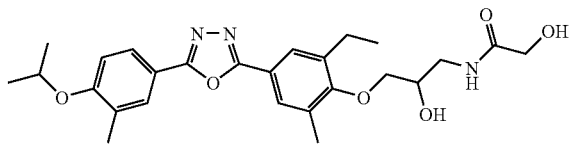

N-(3-{2-Ethyl-4-[5-(4-isopropoxy-3-methyl-phenyl)-[1,3,4]oxadiazol-2-yl]-6-methyl-phenoxy}-2-hydroxy-propyl)-2-hydroxy-acetamide is prepared in analogy to Example 3 starting from 1-amino-3-{2-ethyl-4-[5-(4-isopropoxy-3-methyl-phenyl)-[1,3,4]oxadiazol-2-yl]-6-methyl-phenoxy}-propan-2-ol; LC-MS: $t_R$=0.98 min, $[M+1]^+$=484.24.

Example 27

GTPγS Assay to determine $EC_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM $MgCl_2$ (Fluka, 63064), 0.1% BSA (Calbiochem, 126609), 1 μM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4$/$NaH_2PO_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Table 1 shows the $EC_{50}$ value of some compounds of the present invention. The $EC_{50}$ values were determined according to the method described above:

TABLE 1

| Compound of Example | $EC_{50}$ [nM] |
|---|---|
| 6 | 0.1 |
| 20 | 0.8 |

Example 28

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of a compound of the present invention to normotensive male Wistar rats as compared to a group of animals treated with vehicle only.

TABLE 2

| Compound of Example | Lymphocyte counts |
| --- | --- |
| 9 | −70 ± 2% |

The invention claimed is:
1. A compound of the Formula (I),

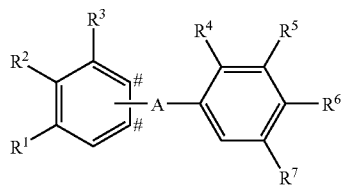

Formula (I)

wherein the symbol # indicates the two carbon atoms of the phenyl ring bearing $R^1$, $R^2$ and $R^3$ to either of which the group A may be attached; and wherein
A represents

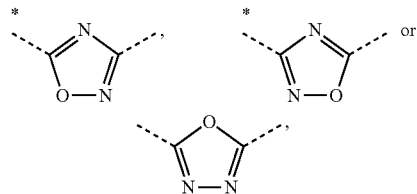

wherein the asterisks indicate the bond that is linked to the phenyl ring of Formula (I) bearing $R^1$, $R^2$, and $R^3$;
$R^1$ represents hydrogen, $C_{1-3}$-alkyl, fluoro, chloro, methoxy, or cyano;
$R^2$ represents $C_{2-5}$-alkyl or $C_{1-4}$-alkoxy;
$R^3$ represents hydrogen, and if group A is attached to the para-position with respect to R2 of the phenyl ring of the Formula (I) bearing $R^1$, $R^2$, $R^3$, then $R^3$ is a H or methyl;
$R^4$ represents hydrogen;
$R^5$ represents methyl, ethyl or methoxy;
$R^6$ represents —$CH_2$—$(CH_2)_k$—$NR^{61}R^{62}$, —$(CH2)_n$CH(OH)—$CH_2$—$NR^{61}R^{62}$, —$CH_2(CH_2)_n$NHSO$_2R^{63}$, —$(CH_2)_n$CH(OH)—$CH_2$—NHSO$_2R^{63}$, —$CH_2$—$(CH_2)_n$—NHCOR$^{64}$, —$(CH_2)_n$CH(OH)—$CH_2$—NHCOR$^{64}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —OCH$_2$—$(CH_2)_m$—NR$^{61}$R$^{62}$, —OCH$_2$—CH(OH)—CH$_2$—NR$^{61}$R$^{62}$, —OCH$_2$—$(CH_2)_m$NHSO$_2$R$^{63}$, —OCH$_2$—CH(OH)—CH$_2$—NHSO$_2$R$^{63}$, —OCH$_2$—$(CH_2)_m$—NHCOR$^{64}$, or —OCH$_2$—CH(OH)—CH$_2$—NHCOR$^{64}$;
$R^{61}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;
$R^{62}$ represents hydrogen, methyl, or ethyl;
$R^{63}$ represents $C_{1-3}$-alkyl, methylamino, ethylamino, or dimethylamino;
$R^{64}$ represents hydroxymethyl, 2-hydroxyethyl, 2-hydroxy-1-hydroxymethyl-ethyl, or 2,3-dihydroxypropyl;
k represents the integer 1, 2, or 3;
m represents the integer 1 or 2;
n represents 0, 1, or 2; and
$R^7$ represents methyl, ethyl or halogen; in free or salt form.
2. The compound according to claim 1, wherein A represents

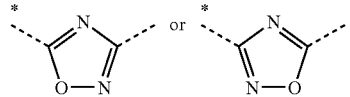

wherein the asterisks indicate the bond that is linked to the phenyl ring of Formula (I) bearing $R^1$, $R^2$, and $R^3$, in free or salt form.
3. The compound according to claim 1, wherein A represents

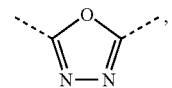

in free or salt form.
4. The compound according to claim 1, wherein $R^1$ represents a methyl group in free or salt form.
5. The compound according to claim 1, wherein $R^2$ represents n-propyl, n-butyl, isobutyl, isoamyl, propoxy or isopropoxy, in free or salt form.
6. The compound according to claim 1, wherein $R^2$ represents isobutyl or isopropoxy, in free or salt form.
7. The compound according to claim 1, wherein $R^3$ represents hydrogen, in free or salt form.
8. The compound according to claim 1, wherein $R^5$ and $R^7$ represent a methyl group, in free or salt form.
9. The compound according to claim 1, wherein $R^5$ represents a methyl group, and $R^7$ represents an ethyl group, in free or salt form.
10. The compound according to claim 1, wherein $R^5$ represents a methoxy group, and $R^7$ represents a chlorine atom, in free or salt form.
11. The A compound according to claim 1, wherein $R^6$ represents —$CH_2$—$(CH_2)_k$—NR$^{61}$R$^{62}$, $(CH_2)_n$CH(OH)—CH$_2$—NR$^{61}$R$^{62}$, —CH$_2$—$(CH_2)_n$—NHCOR$^{64}$, —$(CH_2)_n$CH(OH)—CH$_2$—NHCOR$^{64}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —OCH$_2$—$(CH_2)_m$—NR$^{61}$R$^{62}$, —OCH$_2$—CH(OH)—CH$_2$—NR$^{61}$R$^{62}$, —OCH$_2$—$(CH_2)_m$—NHSO$_2$R$^{63}$, —OCH$_2$—CH(OH)—CH$_2$—NHSO$_2$R$^{63}$, —OCH$_2$—$(CH_2)_m$—NHCOR$^{64}$, or —OCH$_2$—CH(OH)—CH$_2$—NHCOR$^{64}$, in free or salt form.
12. The A compound according to claim 1, wherein $R^6$ represents hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —OCH$_2$—$(CH_2)_m$—NHCOR$^{64}$, or —OCH$_2$—CH(OH)—CH$_2$—NHCOR$^{64}$, in free or salt form.
13. The compound according to claim 1, wherein $R^6$ represents 3-hydroxy-2-hydroxymethyl-propoxy, 2,3-dihydroxypropoxy, or —OCH$_2$—CH(OH)—CH$_2$—NHCOR$^{64}$, in free or salt form.
14. The compound according to claim 1, wherein $R^6$ represents —OCH$_2$—CH(OH)—CH$_2$—NHCOR$^{64}$, and $R^{64}$ represents hydroxymethyl, in free or salt form.

15. The compound according to claim 1, wherein the group A is attached at the para position with respect to $R^2$ to the phenyl ring of Formula (I) bearing $R^1$, $R^2$ and $R^3$, and salt form.

16. The compound according to claim 1,
$R^1$ represents methyl; $R^2$ represents isobutyl or isopropoxy; $R^3$ represents hydrogen; $R^6$ represents 3-hydroxy-2-hydroxymethyl-propoxy, 2,3-dihydroxypropoxy, or —OCH$_2$—CH(OH)—CH$_2$—NHCOR$^{64}$; and $R^7$ represents methyl, ethyl or chlorine; in free or salt form.

17. The compound according to claim 1 selected from the group consisting of:
2-hydroxy-N-((2R)-2-hydroxy-3-{4-[5-(4-isopropoxy-3-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isopropoxy-3-methyl-phenyl)-[1,2,4]oxadiazol-3-yl]-2,6-dimethyl-phenoxy}-propyl)-acetamide,
N-((2R)-3-{2-ethyl-4-[5-(4-isopropoxy-3-methyl-phenyl)-[1,2,4]oxadiazol-3-yl]-6-methyl-phenoxy}-2-hydroxy-propyl)-2-hydroxy-acetamide,
N-((2S)-3-{2-ethyl-4-[5-(4-isopropoxy-3-methyl-phenyl)-[1,2,4]oxadiazol-3-yl]-6-methyl-phenoxy}-2-hydroxy-propyl)-2-hydroxy-acetamide,
2-hydroxy-N-((2R)-2-hydroxy-3-{4-[5-(3-isopropoxy-4-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(3-isopropoxy-4-methyl-phenyl)-[1,2,4]oxadiazol-3-yl]-2,6-dimethyl-phenoxy}-propyl)-acetamide,
2-hydroxy-N-((2R)-2-hydroxy-3-{4-[5-(4-isobutyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isobutyl-phenyl)-[1,2,4]oxadiazol-3-yl]-2,6-dimethyl-phenoxy}-propyl)-acetamide,
2-hydroxy-N-((2R)-2-hydroxy-3-{-4-[5-(4-isobutyl-3-methyl-phenyl)-[1,2,4]oxadiazol-3-yl]-2,6-dimethyl-phenoxy}-propyl)-acetamide,
2-hydroxy-N-((2S)-2-hydroxy-3-{4-[5-(4-isobutyl-3-methyl-phenyl)-[1,2,4]oxadiazol-3-yl]-2,6-dimethyl-phenoxy}-propyl)-acetamide,
N-((2R)-3-{2-ethyl-4-[5-(4-isopropoxy-3-methyl-phenyl)-[1,3,4]oxadiazol-2-yl]-6-methyl-phenoxy}-2-hydroxy-propyl)-2-hydroxy-acetamide, and
N-((2S)-3-{2-ethyl-4-[5-(4-isopropoxy-3-methyl-phenyl)-[1,3,4]oxadiazol-2-yl]-6-methyl-phenoxy}-2-hydroxy-propyl)-2-hydroxy-acetamide, in free or salt form.

18. A pharmaceutical composition comprising a compound according to claim 1, in free or pharmaceutically acceptable salt form, and a pharmaceutically acceptable carrier.

19. The compound according to claim 1, wherein A represents

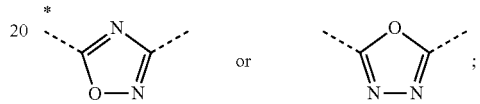

wherein the asterisk indicates the bond that is linked to the phenyl ring of Formula (I) bearing $R^1$, $R^2$, and $R^3$;
$R^1$ represents hydrogen or $C_{1-3}$-alkyl;
$R^5$ represents methyl or ethyl;
$R^6$ represents hydroxy, 2,3-dihydroxypropoxy, —OCH$_2$—CH(OH)—CH$_2$—NR$^{61}$R$^{62}$ or —OCH$_2$—CH(OH)—CH$_2$—NHCOR$^{64}$;
$R^{61}$ and $R^{62}$ both represent hydrogen;
$R^{64}$ represents hydroxymethyl; and
$R^7$ represents methyl or ethyl;
in free or salt form.

* * * * *